(12) United States Patent
Li et al.

(10) Patent No.: US 12,377,042 B2
(45) Date of Patent: *Aug. 5, 2025

(54) BOTANICAL AND BACTERIAL EXTRACTS DISPLAYING RETINOL-LIKE ACTIVITY

(71) Applicant: KENVUE BRANDS LLC, Summit, NJ (US)

(72) Inventors: Wen-Hwa Li, Cranbury, NJ (US); Khalid Mahmood, Lawrenceville, NJ (US); Ramine Parsa, Lawrenceville, NJ (US); Daphne Meza, Hillsborough, NJ (US); Antonius Pieter J. Van Den Heuvel, Willow Grove, PA (US); Teena Varghese, Philadelphia, PA (US); Marina Nelen, Medford, MA (US)

(73) Assignee: Kenvue Brands LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,995

(22) Filed: Aug. 3, 2023

(65) Prior Publication Data

US 2023/0381075 A1    Nov. 30, 2023

Related U.S. Application Data

(63) Continuation of application No. 16/519,207, filed on Jul. 23, 2019.

(60) Provisional application No. 62/703,903, filed on Jul. 27, 2018.

(51) Int. Cl.

| | | |
|---|---|---|
| A61K 8/37 | (2006.01) | |
| A61K 8/36 | (2006.01) | |
| A61K 8/9789 | (2017.01) | |
| A61K 8/99 | (2017.01) | |
| A61K 31/192 | (2006.01) | |
| A61K 31/216 | (2006.01) | |
| A61K 35/74 | (2015.01) | |
| A61K 36/28 | (2006.01) | |
| A61K 36/48 | (2006.01) | |
| A61K 36/54 | (2006.01) | |
| A61K 36/75 | (2006.01) | |
| A61P 17/10 | (2006.01) | |
| A61Q 17/00 | (2006.01) | |
| A61Q 19/08 | (2006.01) | |

(52) U.S. Cl.
CPC ............ *A61K 8/9789* (2017.08); *A61K 8/361* (2013.01); *A61K 8/37* (2013.01); *A61K 8/99* (2013.01); *A61K 31/192* (2013.01); *A61K 31/216* (2013.01); *A61K 35/74* (2013.01); *A61K 36/28* (2013.01); *A61K 36/48* (2013.01); *A61K 36/54* (2013.01); *A61K 36/75* (2013.01); *A61P 17/10* (2018.01); *A61Q 17/00* (2013.01); *A61Q 19/08* (2013.01); *A61K 2800/30* (2013.01); *A61K 2800/75* (2013.01)

(58) Field of Classification Search
None
See application file for complete search history.

(56) References Cited

U.S. PATENT DOCUMENTS

| | | |
|---|---|---|
| 4,193,931 A | 3/1980 | Loeliger |
| 4,691,820 A | 9/1987 | Martinez |
| 4,939,171 A | 7/1990 | Moeller et al. |
| 5,467,868 A | 11/1995 | Abrams et al. |
| 5,488,815 A | 2/1996 | Abrams et al. |
| 5,577,367 A | 11/1996 | Abrams et al. |
| 5,578,312 A | 11/1996 | Parrinello |
| 5,696,686 A | 12/1997 | Sanka et al. |
| 5,704,468 A | 1/1998 | Lust et al. |
| 5,823,327 A | 10/1998 | Wu et al. |
| 6,018,931 A | 2/2000 | Byram et al. |
| 6,050,398 A | 4/2000 | Wilde et al. |
| 6,071,962 A | 6/2000 | Ptchelintsev et al. |
| D435,966 S | 1/2001 | Duis et al. |
| 6,197,343 B1 | 3/2001 | Minami et al. |
| 6,200,594 B1 | 3/2001 | Ernest et al. |
| 7,205,012 B1 | 4/2007 | Hill |
| 7,442,391 B2 | 10/2008 | Koganov |
| 7,452,547 B2 | 11/2008 | Lambino et al. |

(Continued)

FOREIGN PATENT DOCUMENTS

| | | |
|---|---|---|
| CA | 2617255 C | 4/2016 |
| CN | 101336869 A | 1/2009 |

(Continued)

OTHER PUBLICATIONS

Gromkowska-Kepka, Krystyna Joanna et al. The impact of ultraviolet radiation on skin photoaging—review of in vitro studies. Journal of Cosmetic Dermatology. Wiley. 2021;20:3427-3431. (Year: 2021).*

Caithness Biotechnologies Ltd., UK, "Extracts of Calendula officinalis and of Trigonella foenum-graecum", Part of The Phytotitre Natural Product Library website, accessed before Jul. 23, 2019, http://caithnessbiotechnologies.com.

(Continued)

*Primary Examiner* — Nghi V Nguyen
(74) *Attorney, Agent, or Firm* — BakerHostetler (57) ABSTRACT

Provided are botanical or bacterial extracts and methods of treating skin and other tissues by applying certain botanical or bacterial extracts, such as from *Acronychia acidula, Licaria vernicosa, Calendula officinalis, Trigonella foenum-graecum* or *Actimomyces* bacteria, to the skin or other tissue. In particular, provided are methods of treating signs of skin aging, comprising topically applying to skin in need of treatment for signs of skin aging a composition comprising 3-(4-farnesyloxyphenyl)-propionic acid and/or its ethyl ester.

19 Claims, 1 Drawing Sheet

(56) References Cited

U.S. PATENT DOCUMENTS

| | | | |
|---|---|---|---|
| 7,473,435 B2 | 1/2009 | Koganov | |
| 7,537,791 B2 | 5/2009 | Koganov | |
| 8,128,973 B2 | 3/2012 | Mulvanerty | |
| 8,361,516 B2 | 1/2013 | Lintner et al. | |
| 8,470,350 B2 | 6/2013 | Gervasio | |
| 8,496,976 B2 | 7/2013 | Gore et al. | |
| 8,778,420 B1 | 7/2014 | Boyt | |
| 8,828,412 B2 | 9/2014 | Yu et al. | |
| 9,220,928 B2* | 12/2015 | Gordon | A61P 39/06 |
| 9,364,414 B2 | 6/2016 | Domloge et al. | |
| 9,480,645 B2 | 11/2016 | Yu | |
| 9,814,659 B2 | 11/2017 | Loy et al. | |
| 9,925,137 B2 | 3/2018 | Stout et al. | |
| 10,010,572 B2 | 7/2018 | Parris | |
| 2003/0113388 A1 | 6/2003 | Phan | |
| 2003/0165545 A1 | 9/2003 | Huth et al. | |
| 2004/0146539 A1 | 7/2004 | Gupta | |
| 2004/0156873 A1 | 8/2004 | Gupta | |
| 2004/0161435 A1 | 8/2004 | Gupta | |
| 2004/0202638 A1 | 10/2004 | Takada et al. | |
| 2004/0223942 A1 | 11/2004 | Fujimura | |
| 2005/0226834 A1 | 10/2005 | Lambino et al. | |
| 2005/0238613 A1 | 10/2005 | Cals-Grierson et al. | |
| 2006/0110415 A1 | 5/2006 | Gupta | |
| 2006/0133997 A1 | 6/2006 | Querleux et al. | |
| 2007/0184017 A1* | 8/2007 | Faryniarz | A61K 8/361 |
| | | | 424/78.37 |
| 2008/0221064 A1 | 9/2008 | Ueno et al. | |
| 2009/0241242 A1 | 10/2009 | Beatty et al. | |
| 2010/0129296 A1 | 5/2010 | Olsen | |
| 2010/0190734 A1 | 7/2010 | Brazzell et al. | |
| 2011/0077219 A1 | 3/2011 | Conti | |
| 2011/0081372 A1 | 4/2011 | Gervasio | |
| 2011/0110989 A1 | 5/2011 | Simonnet et al. | |
| 2011/0318439 A1 | 12/2011 | Gordon et al. | |
| 2012/0003296 A1 | 1/2012 | Shantha et al. | |
| 2013/0195925 A1 | 8/2013 | Arshed | |
| 2013/0259815 A1* | 10/2013 | Loy | A61K 8/36 |
| | | | 424/62 |
| 2015/0056175 A1 | 2/2015 | Garcia Gilabert | |
| 2015/0250691 A1 | 9/2015 | Piccardi et al. | |
| 2016/0000845 A1 | 1/2016 | Olsen | |
| 2016/0074455 A1 | 3/2016 | Paufique | |
| 2017/0049719 A1 | 2/2017 | Marcy et al. | |
| 2017/0172964 A1 | 6/2017 | Coupland | |
| 2017/0304187 A1 | 10/2017 | Weisenfluh et al. | |
| 2018/0036233 A1 | 2/2018 | Shabaik et al. | |
| 2018/0161263 A1 | 6/2018 | Au et al. | |
| 2019/0008907 A1 | 1/2019 | Al-Waili | |
| 2019/0091122 A1 | 3/2019 | Brun et al. | |
| 2019/0105261 A1 | 4/2019 | Waygh et al. | |
| 2021/0145916 A1 | 5/2021 | Li et al. | |
| 2022/0087965 A1 | 3/2022 | Li et al. | |

FOREIGN PATENT DOCUMENTS

| | | | |
|---|---|---|---|
| CN | 101376016 A | 3/2009 | |
| CN | 101411679 A | 4/2009 | |
| CN | 102307842 A | 1/2012 | |
| CN | 103505389 A | 1/2014 | |
| CN | 103142968 B | 2/2014 | |
| CN | 104042540 A | 9/2014 | |
| CN | 105411960 A | 3/2016 | |
| CN | 106176275 A | 12/2016 | |
| CN | 108852985 A | 11/2018 | |
| CN | 109833267 A | 6/2019 | |
| EP | 0 334 777 A1 | 9/1989 | |
| EP | 904772 B | 9/2003 | |
| EP | 742007 B | 11/2003 | |
| EP | 1303253 B | 9/2004 | |
| EP | 2254544 B | 1/2012 | |
| EP | 2829276 A | 1/2015 | |
| JP | H8133967 A | 5/1996 | |
| JP | H08217620 A | 8/1996 | |
| JP | 2001151633 A | 6/2001 | |
| JP | 2003002813 A | 1/2003 | |
| JP | 2003137767 A | 5/2003 | |
| JP | 2003238432 A | 8/2003 | |
| JP | 2005132793 A | 5/2005 | |
| JP | 2006008537 A | 1/2006 | |
| JP | 2006063038 A | 3/2006 | |
| JP | 2006273811 A | 10/2006 | |
| JP | 2009013128 A | 1/2009 | |
| JP | 4278473 B2 | 6/2009 | |
| JP | 4384261 B | 12/2009 | |
| JP | 2010106000 A | 5/2010 | |
| JP | 2015178489 A | 10/2015 | |
| KR | 20040059006 A | 7/2004 | |
| KR | 2006074038 A | 7/2006 | |
| KR | 2016009330 A | 1/2016 | |
| KR | 2016109360 A | 9/2016 | |
| KR | 2016116733 A | 10/2016 | |
| KR | 2017012810 A | 2/2017 | |
| MX | 2011/013407 A | 6/2013 | |
| RO | 115698 B1 | 3/2002 | |
| RU | 2292887 C2 | 2/2007 | |
| RU | 2014140541 A | 5/2016 | |
| WO | WO-9617589 A1 * | 6/1996 | A61K 8/368 |
| WO | WO 1997/004788 A | 2/1997 | |
| WO | WO 97/39769 A1 | 10/1997 | |
| WO | WO 2002/015860 A | 2/2002 | |
| WO | WO 2005/049048 A | 6/2005 | |
| WO | WO 2007/061200 A1 | 5/2007 | |
| WO | WO 2010/071941 A1 | 1/2010 | |
| WO | WO 2010/111745 A | 10/2010 | |
| WO | WO 2013/171764 A | 11/2013 | |
| WO | WO 2015/099019 A1 | 7/2015 | |
| WO | WO-2015167539 A2 * | 11/2015 | A61K 8/042 |
| WO | WO 2017/013568 A | 1/2017 | |
| WO | WO 2017/053339 A1 | 3/2017 | |
| WO | WO 2017/219582 A | 12/2017 | |
| WO | WO 2018/154145 A | 8/2018 | |
| WO | WO 2020/021475 A2 | 1/2020 | |
| WO | WO 2020/021477 A2 | 1/2020 | |
| WO | WO 2020/021480 A2 | 1/2020 | |

OTHER PUBLICATIONS

Chambron et al., "Interlacing molecular threads on transition metals", *Pure & Appl. Chem.* (1990) 62(6):1027-1034.

Colipa Guideline: Guideline for the Colorimetric Determination of Skin Colour Typing and Prediction of the Minimal Erythema! Dose (MED) Without UV Exposure (2007).

Craig et al., "TFOS DEWS II definition and classification report", *Ocular Surface* (2017) 15:276-283.

De Silva et al., "Demethylacrovestone From Achronychia Pedunculata Fruits", Phytochemistry, (1991), 30(5), pp. 1709-1710.

Dreyfuss et al., "Altered hyaluronic acid content in tear fluid of patients with adenoviral conjunctivitis", *Anais da Academia Brasileira de Ciencias* (2015) 87(1):455-462.

Elma Skin Revitalizer, accessed before Jul. 23, 2019, https://elmaskincare.com/files/P_HT-ELMASR.htm.

International Cosmetic Ingredient Dictionary and Handbook, eds. Wenninger and McEwen, pp. 1626, 1654-1661, and 1673-1686 (The Cosmetic, Toiletry and Fragrance Assoc., Washington, D.C., 7th Edition, 1997.

Laemmli, "Cleavage of structural proteins during the assembly of the head of bacteriophage T4", *Nature* (1970) 227:680-685.

Leigh et al., "Benzylic Imine Catenates: Readily Accessible Octahedral Analogues of the Sauvage Catenates", *Angew. Chem Int. Ed.*, 2001, 40(8):1538-1542.

Li et al., "In vitro modeling of unsaturated free fatty acid-mediated tissue impairments seen in acne lesions", *Arch Dermatol Res*, published on May 31, 2017, Springer-Verlag Berlin Heidelberg 2017.

Maker et al., "Pancreatic cyst fluid and serum mucin levels predict dysplasia in intraductal papillary mucinous neoplasms of the pancreas", *Ann Surg Oncol.* (2011) 18(1):199-206.

Martins et al., "Practical determination of hyaluronan by a new noncompetitive fluorescence-based assay on serum of normal and cirrhotic patients", *Analytical Biochemistry* (2003) 319:65-72.

(56) References Cited

OTHER PUBLICATIONS

Mintel—Fruit Fiesta Peel, MyChelle Dermaceuticals Age Defense, Apr. 2012.
Pacella et al., "Glycosaminoglycans in the human cornea: age-related changes", Ophthalmol. Eye Dis. (2015) 7:1-5.
SkinlightCo.uk: "Skin Brightening Fruit Fiesta Peel," (URL:http://www.skinlight.co.uk/product.sub.--845.sub.--Skin+Brightening+-Fruit+Fiesta+Peel+.html—Jan. 1, 2006).
Solano et al., "Hypopigmenting agents: an updated review on biological, chemical and clinical aspects", Pigment Cell Res. (2006) 19:550-571.
Su et al., "Acetophenone Derivatives from Acronychia pedunculata", Journal of Natural Products, (2003), 66(7) pp. 990-993.
Tanimoto, Shinichi et al., "Synthesis and Cosmetic Whitening Effect of Glycosides Derived from Several Phenylpropanoids", Yakugaku Zasshi=Journal of the Pharmaceutical Society of Japan, JP, vol. 126, No. 3, Mar. 1, 2006, pp. 173-177, XP009081014, ISSN: 0031-6903, DOI: 10 1248/Yakushi. 126.173.
Toshida et al., "The Effectsof Vitamin A Compounds on Hyaluronic Acid Released from Cultured Rabbit Corneal Epithelial Cells and Keratocytes", J Nutr Sci Vitaminol (2012) 58:223-229.
Uchino et al., "Alteration of Tear Mucin 5AC in Office Workers Using Visual Display Terminals: The Osaka Study", JAMA Ophthalmol. (2014) 132(8):985-992.
Zuo Xia Lin et al., "Application of Free Radical Scavenger in Cosmetics", the 11$^{th}$ Southeast Asia Cosmetic Medicine Academic Conference, pp. 29-31, Dec. 31, 2009 (Reference translation—may contain inconsistencies).
ID#: 1563580, Database Mintel [online], 2011, retrieved from http://www.gnpd.com—Nourish & Polish Skin Collection (Kosmea).
Novoseletsky Jennifer, Cosmetics & Toiletries, 2016, [retrieved on Apr. 21, 2023], retrieved from the Internet, URL: https://www.cosmeticsandtoiletries.com/cosmetic-ingredients/actives/news/21845199/a-range-of-wonder-from-down-under.
Jadoon S. et al., "Anti-Aging Potential of Phytoextract Loaded-Pharmaceutical Creams for Human Skin Cell Longevity".
Gromkowska-K pka, Krystyna Joanna et al. The impact of ultraviolet radiation on skin photoaging—review of in vitro studies. Journal of Cosmetic Dermatology. Wiley. 2021 ;20:3427-3431. (Year: 2021). http://www.360doc.com/content/17/0914/10/17962130_687080205.
Harkevič D.A., Farmakologiâ [Pharmacology], 10th ed., M .: GEOTAR-Media, 2010, pp. 73-74 ( translation).
Murav'eva D.A.: Farmakognoziâ(s osnovami biohimii lekarstvennyh rastenij) [Pharmacognosy (with Fundamentals of Biochemistry of Medicinal Plants)]: Textbook.—Medicine, 1978, pp. 23,61.
Muraškina I.A. et al.: Tehnologiâ lečebno-kosmetičeskih sredstv [Technology of Medicinal and Cosmetic Products] // Textbook of FGBOU VO IGMU [Federal State Budgetary Educational Institution of Higher Education "Irkutsk State Medical University"] of the Ministry of Health of Russia, Department of Pharmacognosy and Pharmaceutical Technology.—Irkutsk: IGMU, 2021.—p. 111 (pp. 16-19, 100, 102).
V.D. Ponomarev: Èkstragirovanie lekarstvennogo syr'â [Extraction of Medicinal Raw Materials], Moscow, Medicine, 1976, pp. 115-120.
Belikov, V.G., Pharmaceutical Chemistry, Moscow, Vysshaya Shkola, 1993, pp. 43-47. (Machine Translation).
Kharkevich, D.A., Pharmacology: Textbook, 9$^{th}$ Edition, revised and corrected, Moscow, GEOTAR Media, 2008, pp. 66-67. (Machine Translation).
Epifano, F., et al, Phytochemistry and pharmacognosy of the genus Acronychia, Phytochemistry, 2013, 95:12-8, Abstract.
International Search Report, PCT/IB2019/056337 dated Mar. 20, 2020.
El-Nekeety Aziza A et al., "Evaluation of the bioactive extract of actinomyces isolated from the Egyptian environment against aflatoxin B1-induce cytotoxicity, genotoxicity and oxidative stress in the liver of rats." Food and Chemical Toxicology, Pergamon, GB, vol. 105, Apr. 23, 2017 pp. 241-255.
Elmallah Mohammed I Y et al., "Marine actinomycete crude extracts with potent TRAIL-resistance overcoming activity against breast cancer cells." Oncology Reports Jun. 2017, vol. 37, No. 6, pp. 3635-3642.
Takemura Maki et al., "Canaliculitis caused by Actinomyces in a case of dry eye with punctal plug occlusion." Nippon Ganka Gakkai Zasshi Jul. 2002, vol. 106, No. 7, pp. 416-419.
Bowen, P., "Particle Size Distribution Measurement from Millimeters to Nanometers and from Rods to Platelets," Journal of Dispersion Science and Technology, Taylor and Francis Group, New York, NY, vol. 23, No. 5, Jan. 1, 2002, pp. 631-662. (XP009102859).
Extended EP Search Report, EP 20208677.3-1112, dated Apr. 15, 2021.
International Search Report, PCT/IB2019/056335; dated Jan. 31, 2020.
Ratan Chaudhuri: "Bakuchiol: A Retinol-Like Functional Compound, Modulating Multiple Retinol and Non-Retinol Targets" In: "Cosmeceuticals and Active Cosmetics, Third Edition," Aug. 27, 2015.
Muhammad Nadeem Aslam, et al. "Padma 28: A Multi-Component Herbal Preparation with Retinoid-Like Dermal Activity but Without Epidermal Effects," Journal of Investigative Dermatology; vol. 124, No. 3, Mar. 1, 2005, pp. 524-529.
Mintel—Feb. 14, 2011, "Sleeping Mask."
Mintel—Feb. 14, 2011, "2/1 Eye Cream."
Mintel—Jun. 28, 2007, "Loaded The Anti-Ager."
Mintel—May 22, 2017, "Sensitive Body Lotion."
Mintel—Aug. 26, 2009—"Eye Drops."
Lucas Meyer; "SouthernCross Botanicals," Nov. 19, 2014, pp. 1-20 retrieved from Internet: https://in-cosmetics.com/_novadocuments/245955?v=636017775273900000.
Kaercher T., et al.; "The use of compresses as a supplementary therapy for hyposecretory and hyperevaporative keratoconjunctivitis sicca"; Spektrum Der Augenheilkunde; vol. 16, No. 4, Aug. 1, 2002; pp. 164-169.
Amiram El-Ganiny, et al.; "Prevention of Bacterial Biofilm Formation on Soft Contact Lenses Using Natural Compounds"; Journal of Ophthalmic Inflammation and Infection; BioMed Central Ltd.; vol. 7, No. 1, Apr. 18, 2017; pp. 1-7.
Eric Carlson, et al.; "Impact of Hyaluronic Acid-Containing Artificial Tear Products on Reepithelialization in an In Vivo Corneal Wound Model"; Journal of Ocular Pharmacology and Therapeutics; vol. 34, No. 4, May 1, 2018; pp. 360-364.
Shizuka Koh; "Clinical utility of 3% diquafosol ophthalmic solution in the treatment of dry eyes"; Clinal Ophthalmology; May 1, 2015, p. 865.
Dominique Lesueur, et al.; Composition and antimicrobial activity of the essential oil of Acronychia pedunculata; (L.) Miq .; Natural Product Research; vol. 22, vol. 5, Mar. 20, 2008; pp. 393-398.
Himejima, Masaki, et al., "Antimicrobial Agents from Licaria puchuri-major and Their Synergistic Effect with Polygodial," Journal of Natural Products, vol. 55, No. 5, May 1, 1992, pp. 620-625.
Efstratiou, Efstratios, et al., "Antimicrobial activity of petal extracts against fungi, as well as Gram-negative and Gram-positive clinical pathogens," Complementary Therapies in Clinical Practice, vol. 18, No. 3, 2012, pp. 173-176.
Gagliano, Caterina, et al., "ARVO Annual Meeting Abstract: Effect of Fenugreek on Severe Evaporative Dysfunctional Tear Syndrome, IOVS, ARVO Journals," Investigative Ophthalmology and Visual Science, Mar. 1, 2012, p. 2, paragraph 1; figure 1.
Scuderi, Gianluca et al., "Effects of phytoestrogen supplementation in postmenopausal women with dry eye syndrome: a randomized clinical trial," Canadian Journal of Ophthalmology, vol. 47, No. 6, Dec. 1, 2012, pp. 489-492.
Blavin, Julia et al., "A Comparison of Azithromycin and Tobramycin Eye Drops on Epithelial Wound Healing and Tolerance After Penetrating Keratoplasty," Journal of Ocular Pharmacology and Therapeutics, vol. 28, No. 4, Aug. 1, 2012, pp. 428-432.

(56) References Cited

OTHER PUBLICATIONS

Toshida, Hiroshi et al., "Efficacy of retinol palmitate eye drops for dry eye in rabbits with lacrimal gland resection," Clinical Ophthalmology, Oct. 1, 2012, p. 1585.
Driot, J.Y. et al., Beneficial effects of a retinoic acid analog, CBS-211 A, on an experimental model of keratoconjunctivitis sicca, Investigative ophthalmology & visual science, Jan. 1, 1992, p. 190.
Loeliger, P., et al., "Arotinoids, A New Class of Highly Active Retinoids," European Journal of Medicinal Chemistry, vol. 15, No. 1, Jan. 1, 1980, pp. 9-15.
International Search Report, PCT/IB2019/056344 dated Nov. 3, 2020.
Invitation to Pay Additional Fees/Partial International Search Report PCT/IB2019/056344 dated Nov. 28, 2019.
Invitation to Pay Additional Fees/Partial International Search Report PCT/IB2019/056337 dated Nov. 27, 2019.
U.S. Appl. No. 11/197,841, filed Dec. 14, 2021, Wen-Hwa Ting Li.
Journal of Ethnopharmacology, 2017, vol. 196, pp. 94-103.
Journal of Japanese Cosmetic Science Society, 2013, vol. 37, No. 1, pp. 11-16.
Highlights of prescribing information label, "TRI-LUMA® (fluocinolone acetonide, hydroquinone, and tretinoin)", Mar. 2014, 10pp.
Ren et al., "Natural Modulators of Key Signaling Pathways in Skin Inflammageing", Clinical, Cosmetic and Investigational Dermatology 2024:17 2967-2988.
Tesfamariam et al., "Awareness, Perception, and Utilization of Skin Lightening Agents Among Females of Asmara, Eritrea: A Cross-Sectional Study", Clinical, Cosmetic and Investigational Dermatology 2023:16 1191-1202.

* cited by examiner

BOTANICAL AND BACTERIAL EXTRACTS DISPLAYING RETINOL-LIKE ACTIVITY

CROSS-REFERENCE TO RELATED APPLICATIONS

This application is continuation of U.S. application Ser. No. 16/519,207 filed Jul. 23, 2019, which claims the benefit of U.S. provisional application No. 62/703,903 filed on Jul. 27, 2018, complete disclosures of which are hereby incorporated herein by reference for all purposes.

FIELD OF INVENTION

The invention relates to compositions having retinol-like activity and methods of using the compositions to treat the human tissue including skin, hair, nails, oral mucosa, nasal mucosa, vaginal mucosa and the like.

DESCRIPTION OF RELATED ART

The human skin is subject to certain aging processes, some of which are attributable to intrinsic processes (e.g. chrono-aging) and some of which are attributable to exogenous factors (e.g. photo-aging). In addition, temporary or even lasting changes to the skin can occur, such as acne, greasy or dry skin, keratoses, rosacea, light-sensitive, inflammatory, erythematous, and allergic or autoimmune-reactive reactions, such as dermatosis and photodermatosis.

The consequences of the above-mentioned ageing processes can include thinning of the skin, weaker interlacing of epidermis and dermis, and a reduction in the number of cells and the supplying blood vessels. This often results in the formation of fine lines and wrinkles, and pigment defects can occur.

Retinoids have been used for treating skin conditions caused by intrinsic aging, exogenous factors, or skin diseases. However, despite the beneficial effects of retinoid treatment, its benefits are limited due to skin irritation of retinoids. These side effects can restrict the use of retinoids. All retinoids used in cosmetic products are synthetic in origin and there is a great demand by the users of cosmetic products to have natural compounds having retinol-like activity and benefits to treat skin.

To date, the search for alternative or natural compounds to replace retinoids has produced limited success in treating skin conditions associated with aging, such as skin atrophy, photo-aging, and in reducing the appearance of wrinkles, fine lines, stretch marks, or cellulite.

U.S. Pat. No. 9,220,928 assigned to Ecobiotics LTD., discloses compounds derived from botanicals of the genus *Acronychia*, including 3-(4-farnesyloxyphenyl)-propionic acid, for use as antioxidants, antibacterials, anthelmintics, anti-inflammatories, cancer chemopreventatives, food additives and/or fragrances components. The patent does not, however, identify any anti-aging properties associated with the compositions therein.

U.S. Patent Publication No. 2013/0259815 assigned to Johnson & Johnson Consumer Companies, Inc., discloses methods of lightening skin by applying certain aromatic compounds or botanical extracts, including plants of the genus *Acronychia*, containing such compounds to the skin.

Applicants have discovered that certain extracts unexpectedly exhibit retinol-like bioactivity and/or other consumer-desirable properties for use on skin and other human tissue, including botanical extracts from plants of the genera *Acronychia, Licaria, Calendula,* and *Trigonella*, and bacterial extracts of the genus *Actinomyces*. Such extracts may be used on skin to provide significant anti-aging, skin barrier improvement and moisturization, anti-acne and other benefits normally associated with retinol. Such extracts may also be used on, for example, oral mucosa, nasal mucosa and vaginal mucosa.

The invention relates to extracts that display retinol-like bioactivities, e.g. in the skin, including upregulation of retinol-responsive genes such as RARg, CRABP2, HbEGF, HAS3, and UGCG in human skin explant culture. Furthermore, the invention relates to methods of treating signs of aging, improving skin barrier function, and providing anti-acne benefits with such botanical or bacterial extracts.

SUMMARY OF THE INVENTION

The invention relates to a method of treating signs of skin aging, comprising topically applying to skin in need of treatment for signs of skin aging a composition comprising an extract selected from the group consisting of extracts of *Acronychia acidula*, extracts of *Licaria vernicosa*, extracts of *Calendula officinalis*, extracts of *Trigonella foenum-graecum*, extracts of *Actimomyces* bacteria, and combinations thereof.

The invention also relates to method of improving skin barrier properties, comprising topically applying to skin in need of improved skin barrier function and moisturization a composition comprising an extract selected from the group consisting of extracts of *Acronychia acidula*, extracts of *Licaria vernicosa*, extracts of *Calendula officinalis*, extracts of *Trigonella foenum-graecum*, extracts of *Actimomyces* bacteria, and combinations thereof.

The invention further relates to method of treating acne, comprising topically applying to skin in need of treatment for acne a composition comprising an extract selected from the group consisting of extracts of *Acronychia acidula*, extracts of *Licaria vernicosa*, extracts of *Calendula officinalis*, extracts of *Trigonella foenum-graecum*, extracts of *Actimomyces* bacteria, and combinations thereof.

The invention relates to a method of treating signs of skin aging, comprising topically applying to skin in need of treatment for signs of skin aging a composition comprising an extract of *Acronychia acidula*.

The invention also relates to a method of improving skin barrier properties, comprising topically applying to skin in need of improved skin barrier function and moisturization a composition comprising an extract of *Acronychia acidula*.

The invention further relates to a method of treating acne, comprising topically applying to skin in need of treatment for acne a composition comprising an extract of *Acronychia acidula*.

The invention also relates to a method of treating signs of skin aging, comprising topically applying to skin in need of treatment for signs of skin aging a composition comprising an extract of *Licaria vernicosa*.

The invention also relates to a method of improving skin barrier properties, comprising topically applying to skin in need of improved skin barrier function and moisturization a composition comprising an extract of *Licaria vernicosa*.

The invention further relates to a method of treating acne, comprising topically applying to skin in need of treatment for acne a composition comprising an extract of *Licaria vernicosa*.

The invention also relates to a method of treating signs of skin aging, comprising topically applying to skin in need of treatment for signs of skin aging a composition comprising an extract of *Calendula officinalis*.

The invention also relates to a method of improving skin barrier properties, comprising topically applying to skin in need of improved skin barrier function and moisturization a composition comprising an extract of *Calendula officinalis*.

The invention further relates to a method of treating acne, comprising topically applying to skin in need of treatment for acne a composition comprising an extract of *Calendula officinalis*.

The invention also relates to a method of treating signs of skin aging, comprising topically applying to skin in need of treatment for signs of skin aging a composition comprising an extract of *Trigonella foenum-graecum*.

The invention also relates to a method of improving skin barrier properties, comprising topically applying to skin in need of improved skin barrier function and moisturization a composition comprising an extract of *Trigonella foenum-graecum*.

The invention further relates to a method of treating acne, comprising topically applying to skin in need of treatment for acne a composition comprising an extract of *Trigonella foenum-graecum*.

The invention also relates to a method of treating signs of skin aging, comprising topically applying to skin in need of treatment for signs of skin aging a composition comprising an extract of *Actimomyces* bacteria.

The invention also relates to a method of improving skin barrier properties, comprising topically applying to skin in need of improved skin barrier function and moisturization a composition comprising an extract of *Actimomyces* bacteria.

The invention further relates to a method of treating acne, comprising topically applying to skin in need of treatment for acne a composition comprising an extract of *Actimomyces* bacteria.

DETAILED DESCRIPTION OF THE INVENTION

It is believed that one skilled in the art can, based upon the description herein, utilize this invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention pertains. Also, all publications, patent applications, patents, and other references mentioned herein are incorporated by reference. As used herein, all percentages are by weight/volume of the total composition unless otherwise specified.

Terms

As used herein, a composition that is "essentially free" of an ingredient means the composition contains about 2% or less of that ingredient by weight based on the total weight of the composition. In one embodiment, a composition that is essentially free of an ingredient contains about 1% or less, preferably about 0.5% or less, more preferably about 0.1% or less, more preferably about 0.05 or less, more preferably about 0.01% or less, by weight based on the total weight of composition of the ingredient. In certain embodiments, a composition that is essentially free of an ingredient is free of the ingredient, i.e. has none of that ingredient in the composition.

As used herein, "cosmetically acceptable" means that the ingredients which the term describes are suitable for use in contact with tissues (e.g., the skin or hair) without undue toxicity, incompatibility, instability, irritation, allergic response, and the like. As will be recognized by one of skill in the art, cosmetically acceptable salts are acidic/anionic or basic/cationic salts. Cosmetically acceptable salts from inorganic bases include, for example, sodium or potassium salts, and the like. Cosmetically acceptable salts from organic bases include, for example, salts formed with primary, secondary, or tertiary amines, and the like.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, the term "safe and effective amount" means an amount sufficient to induce the desired effect, but low enough to avoid serious side effects. The safe and effective amount of a compound, extract, or composition will vary with e.g., the age, health and environmental exposure of the end user, the duration and nature of the treatment, the specific compound, extract, ingredient, or composition employed, the particular cosmetically-acceptable carrier utilized, and like factors.

As used herein, "treatment" or "treating" means the amelioration, prophylaxis, or reversal of a condition, disease, or disorder, or at least one discernible symptom thereof. In one embodiment, "treatment" or "treating" refers to an amelioration, prophylaxis, or reversal of at least one measurable physical parameter related to the condition, disease, or disorder being treated, not necessarily discernible in or by the subject being treated. In another embodiment, "treatment" or "treating" refers to inhibiting or slowing the progression of a condition, disease, or disorder, either physically, e.g., stabilization of a discernible symptom, physiologically, e.g., stabilization of a physical parameter, or both. In another embodiment, "treatment" or "treating" refers to delaying the onset of a condition, disease, or disorder.

In certain embodiments, a composition of the invention is administered as a preventative measure. As used herein, "prevention" or "preventing" refers to a reduction of the risk of acquiring a given condition, disease, or disorder.

Compositions of the present invention are suitable for treating or preventing signs of skin aging. As used herein "signs of skin aging" include the presence of lines and wrinkles, loss of elasticity, uneven skin, and blotchiness. In a particularly preferred embodiment, the sign of aging is the presence of lines and wrinkles and/or loss of elasticity.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

Compositions of the invention are suitable for improving the texture of skin or improving the firmness of skin.

As used herein, "improving the texture of skin" means the smoothing of the surface of the skin to remove either bumps or crevasses on the skin surface.

As used herein, "improving the firmness of skin" means the enhancing of the firmness or elasticity of the skin, preventing the loss of firmness or elasticity of skin, or preventing or treating sagging, lax and loose skin.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "age spots" means a condition of the skin associated with discrete pigmentation, e.g., small areas of darker pigmentation that may develop on the face as well as the hands.

Signs of skin aging also include the presence of diminished skin thickness, and abnormal or diminished synthesis of collagen, glycosaminoglycans, proteoglycans, elastin, or glycoproteins including fibronectin. In one embodiment, the sign of aging is selected from the abnormal or diminished synthesis of collagen, glycosaminoglycans, proteoglycans, elastin, or glycoproteins including fibronectin. In another embodiment, the sign of skin aging is diminished synthesis of collagen or elastin.

The compositions are also suitable for treating or preventing acne. As used herein, "acne" refers to disorders resulting from the actions of hormones and other substances on the sebaceous glands and hair follicles, typically leading to clogged pores and the formation of inflammatory or non-inflammatory lesions on the skin. Specifically, it relates to blemishes, lesions, or pimples, pre-emergent pimples, blackheads, and/or whiteheads. As used herein, a "pre-emergent pimple" is an inflamed follicle that is not visually apparent on the surface of the skin with the naked eye (e.g., as a lesion).

The compositions of the invention are also suitable for treating or preventing rosacea. As used herein, "rosacea" means skin with persistent erythema with or without papules, pustules, or nodules.

The compositions of the invention are also suitable for treating skin in need of improved skin barrier function and moisturization. As used herein, "skin in need of improved skin barrier function and moisturization" means skin that is, but not limited to, lacking in moisture, lacking in sebum, cracked, dry, itchy, scaly, xerodermic, dehydrated, lacks suppleness, lacks radiance, dull, or lacks lipids.

The compositions of the invention are also suitable for enhancing the endogenous hyaluronic acid ("HA") levels in skin, providing improvements in hydration and the appearance of at least one sign of skin aging. Topical use of the composition can increase the levels of hyaluronic acid to a direction found in younger skin thereby providing the structural support to skin to reduce the appearance of signs of aging in skin.

The compositions of the invention are also suitable for reducing epidermal hyperkeratinzation. Accordingly, the composition may be used for treatment or prevention of conditions characterized by hyperkeratinzation, such as acne or warts.

The compositions are also suitable for treating or preventing such skin conditions as cutis laxa (elastin-related disease), sclerosis/scleroderma (collagen-related disease), keratosis pilaris, cellulite, stretch marks, psoriasis, warts, Kaposi's sarcoma, and cutaneous T-cell lymphoma.

The compositions of the invention are also suitable for application to oral mucosa. The compositions may be applied to oral mucosa in need of increased induction of mucins, increased induction of hyaluronic acid, improved barrier, or improved tight junction.

The compositions are further suitable for treatment or prevention of asthma, allergy and itch. For example, the compositions may be applied topically to skin or intranasally to nasal mucosa for such purposes.

Botanical Extracts

We have unexpectedly identified botanical extracts having retinol-like bioactivity. The extracts are obtained from botanicals including, for example, plants of the genera *Acronychia*, *Licaria*, *Calendula*, and *Trigonella*.

Plants of the genus *Acronychia* include, for example, *Acronychia aberrans*, *Acronychia acidula*, *Acronychia acronychioides*, *Acronychia acuminate*, *Acronychia baeuerlenii*, *Acronychia chooreechillum*, *Acronychia crassipetala*, *Acronychia eungellensis*, *Acronychia imperforate*, *Acronychia laevis*, *Acronychia laurifolia*, *Acronychia littoralis*, *Acronychia oblongifolia*, *Acronychia octandra*, *Acronychia parviflora*, *Acronychia pauciflora*, *Acronychia pedunculata*, *Acronychia pubescens*, *Acronychia* species (*Batavia Downs*), *Acronychia suberosa*, *Acronychia vestita*, and *Acronychia wilcoxiana*.

In one embodiment, the extract is obtained from *Acronychia acidula*. The common names for *Acronychia acidula* are lemon aspen, hard aspen and lemonwood. The Latin synonym names for *Aconychia acidua* are *Jambolifera acidula* and *Acronychia superba*.

Plants of the genus *Licaria* include, for example, *Licaria vernicosa*, *Licaria brittoniana*, *Licaria canella*, *Licaria cubensis*, *Licaria yelutina* and *Licaria triandra*. There are about 40 species of genus *Licaria* reported and are endemic to Central and South Americas.

In one embodiment, the extract is obtained from *Licaria vernicosa*.

Plants of the genus *Calendula* include 15-20 species, for example, *Calendula officinalis*. The known synonyms of *Calendua officinalis* are *Calendula aurantiaca*, *Calendula eriocarpa*, *Calendula hydruntina*, *Calendula prolifera*, *Calendula x santamariae*, and *Caltha officinalis*.

In one embodiment, the extract is obtained from *Calendula officinalis*. The common names for *Calendula officinalis* are pot marigold, ruddles, common marigold and Scotch marigold.

Plants of the genus *Trigonella* include 36 known species, for example *Trigonella foenum-graecum*, *Trigonella balansae*, *Trigonella corniculata*, *Trigonella maritima*, *Trigonella spicata*, *Trigonella caerulea*, *Trigonella occulta*, *Trigonella polycerata*, *Trigonella Calliceras*, and *Trigonella Cretica*. *Trigonella foenum-graecum* or the herb fenugreek is the best-known member of the genus *Trigonella*.

In one embodiment, the extract is obtained from *Trigonella foenum-graecum*. The common names for *Trigonella foenum-graecum* are fenugreek, Greek hay, Greek clover, bird's foot, fenugrec, hu lu ba, *trigonella* and bockshornklee.

Any of a variety of extracts of *Acronychia*, *Licaria*, *Calendula*, or *Trigonella* may be used. One extract or a combination of extracts may be used.

The extract may be obtained from any part of the plant such as the fruit, the seed, the bark, the leaf, the flower, petals, the roots and the wood. In certain embodiments, the extract is obtained from the fruit, wood, petals, or leaves of the plant.

In one embodiment, the extract is from the fruit of *Acronychia acidula*.

In another embodiment, the extract is from *Licaria vernicosa* wood.

In a further embodiment, the extract is from *Licaria vernicosa* root.

In another embodiment, the extract is from *Calendula officinalis* petals.

In another embodiment, the extract is from *Trigonella foenum-graecum* leaves.

In certain embodiments, the *Acronychia* and/or *Licaria* extracts useful in the present invention comprise compounds of the following Formula:

wherein:
- $R_1$ is selected from the group consisting of $C_1$-$C_{20}$ alkyl, $C_2$-$C_{20}$ alkenyl, $C_2$-$C_{20}$ alkynyl, and $C_3$-$C_8$ cycloalkyl or aryl;
- $R_2$ is selected from the group consisting of hydrogen, hydroxyl, $C_1$-$C_6$ alkyl, $C_2$-$C_6$ alkenyl, $C_2$-$C_6$ alkynyl, $C_3$-$C_8$ cycloalkyl or aryl, —$OC_1$-$C_6$ alkyl, —$OC_2$-$C_6$ alkenyl, —$OC_2$-$C_6$ alkynyl, —$OC_3$-$C_8$ cycloalkyl or aryl, thiol, —$SC_1$-$C_6$ alkyl, —$SC_2$-$C_6$ alkenyl, —$SC_2$-$C_6$ alkynyl, —$SC_3$-$C_8$ cycloalkyl or aryl, —$NR_4C_1$-$C_6$ alkyl, —$NR_4C_2$-$C_6$ alkenyl, —$NR_4C_2$-$C_6$ alkynyl, and —$NR_4C_3$-$C_8$ cycloalkyl or aryl;
- $R_3$ is selected from —$CO_2H$, —$CO_2R_4$ or an isosteric equivalent of a carboxy group, wherein $R_4$ is $C_1$-$C_6$ alkyl, $C_2$-$C_6$ alkenyl, $C_3$-$C_8$ cycloalkyl or aryl; and
- Y is —($CH_2$—$CH_2$)—, —(CH=CH)—, or —(C≡C)—;

or a cosmetically acceptable salt thereof.

In certain embodiments, the *Acronychia* and/or *Licaria* extracts useful in the present invention comprise compounds of the Formula:

wherein:
- $R_1$ is selected from the group consisting of $C_5$-$C_{16}$ alkyl, $C_5$-$C_{16}$ alkenyl, and $C_5$-$C_{16}$ alkynyl, more preferably $C_5$-$C_{16}$ alkenyl, including, for example, farnesyl;
- $R_2$ is selected from the group consisting of hydrogen, hydroxyl, —$OC_1$-$C_6$ alkyl, —$OC_2$-$C_6$ alkenyl, —$OC_2$-$C_6$ alkynyl, —$OC_3$-$C_8$ cycloalkyl, more preferably hydrogen, hydroxyl, —$OC_1$-$C_6$ alkyl, even more preferably hydrogen or —$OC_1$-$C_3$ alkyl;
- $R_3$ is selected from —$CO_2H$, —$CO_2R_4$ wherein $R_4$ is $C_1$-$C_6$ alkyl, or an isosteric equivalent of a carboxy group; and
- Y is —($CH_2$—$CH_2$)— or —(CH=CH)—;

or a cosmetically acceptable salt thereof.

In certain embodiments, at least one compound of the above Formula is present in the extract the *Acronychia* and/or *Licaria* at a concentration equal to or greater than 1% (or about 1%) to about 20%, or optionally from about 7% (or about 7%) to about 10% (or about 10%), by weight of the *Acronychia* and/or *Licaria* extract.

In certain embodiments, the compounds of the above Formula are in the form of an acid or alkylester selected from (or, selected from the group consisting of) 3-(4-farnesyloxyphenyl)-propionic acid, 3-(4-farnesyloxy-3-hydroxyphenyl)-propionic acid, 3-(4-farnesyloxy-3-methoxyphenyl)-propionic acid, alkylesters thereof, in particular ethyl esters thereof, and combinations of two or more thereof.

In certain embodiments, the compound of the above Formula is 3-(4-farnesyloxyphenyl)-propionic acid and/or its ethyl ester.

In certain embodiments, the 3-(4-farnesyloxyphenyl)-propionic acid and/or its ethyl ester is present in the extract the *Acronychia* and/or *Licaria* at a concentration equal to or greater than 1% (or about 1%) to about 20%, or optionally from about 7% (or about 7%) to about 10% (or about 10%), by weight of the *Acronychia* and/or *Licaria* extract.

The 3-(4-farnesyloxyphenyl)-propionic acid and/or its ethyl ester can be synthesized using conventional organic synthesis processes.

Accordingly, in one embodiment, a composition comprising 3-(4-farnesyloxyphenyl)-propionic acid and/or its ethyl ester is used. Such a composition may be used in any of the methods of the invention. In certain embodiments, the composition may comprise equal to or greater than 1% (or about 1%) to about 20%, or optionally from about 7% (or about 7%) to about 10% (or about 10%), by weight of 3-(4-farnesyloxyphenyl)-propionic acid and/or its ethyl ester based on the total weight of the composition.

Suitable extracts may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like.

Any of a variety of solvents including polar solvents, non-polar solvents, or combinations of two or more thereof may be used in methods comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids.

In one embodiment, the extract comprises an extract of *Acronychia acidula*. In another embodiment, the extract of the invention comprises a combination of polar and non-polar extracts of *Acronychia acidula* fruit. In another embodiment, the extract of the invention comprises alcoholic or glycolic extracts of *Acronychia acidula* fruit.

In one embodiment, the extract comprises an extract of *Licaria vernicosa*. In another embodiment, the extract of the invention comprises a combination of polar and non-polar extracts of *Licaria vernicosa* wood or *Licaria vernicosa* root. In another embodiment, the extract of the invention comprises alcoholic extracts of *Licaria vernicosa* wood or *Licaria vernicosa* root.

In another embodiment, the extract is a polar extract prepared using a polar solvent comprising water, $C_1$-$C_8$ alcohols, $C_1$-$C_8$ polyols, or $C_1$-$C_8$ glycols, or combinations of two or more thereof. In certain embodiments, the extract is extracted using one or more $C_1$-$C_4$ alcohols, $C_1$-$C_4$ polyols, and/or $C_1$-$C_4$ glycols. In certain embodiments, the extract is prepared using a solvent comprising methanol, ethanol, or a combination thereof with or without presence of water.

In another embodiment, the extract is a polar extract extracted from *Acronychia acidula* fruit using a combination of alcohol and water.

In yet another embodiment, the extract is a polar extract extracted from ground (i.e., reduced to small particles) wood of *Licaria vernicosa*, or ground root of *Licaria vernicosa* using methanol.

In one embodiment, the extract comprises an extract of *Calendula officinalis*. In another embodiment, the extract of the invention comprises a combination of polar and non-polar extracts of *Calendula officinalis* petals. In another embodiment, the extract of the invention comprises a non-polar extract of *Calendula officinalis* petals.

In one embodiment, the extract comprises an extract of *Trigonella foenum-graecum*. In another embodiment, the extract of the invention comprises a combination of polar and non-polar extracts of *Trigonella foenum-graecum* leaves. In another embodiment, the extract of the invention comprises a non-polar extract of *Trigonella foenum-graecum* leaves.

In yet another embodiment, the extract is a non-polar extract prepared using a non-polar solvent comprising one or more $C_1$-$C_8$ alkanes, $C_1$-$C_8$ cycloalkanes, $C_1$-$C_8$ alkyl ethers, $C_1$-$C_8$ alkyl esters and/or chloroform, more preferably one or more $C_1$-$C_8$ alkanes, $C_1$-$C_8$ alkyl esters and/or chloroform.

In yet another embodiment, extract is a non-polar extract prepared using hexanes, ethyl acetate, chloroform, or mixtures of two or more thereof. In yet another embodiment, the extract is a non-polar extract prepared using ethyl acetate.

In one embodiment, the botanical extracts may be obtained via extraction of cell cultures of various plants, including cell cultures of the genera *Acronychia, Licaria, Calendula,* or *Trigonella*. The cell cultures which are extracted to obtain botanical extracts for use in the invention may be of any form including suspension cell cultures and the like.

Bacterial Extracts

We have unexpectedly identified bacterial extracts having retinol-like bioactivity. Bacteria of the genus *Actinomyces* include many species fully characterized, as well as some of them which are not well characterized, for example one species collected from USA and labeled species as A5640. A sample of this bacteria is collected, grown in culture and made into an extract. The extract is a part of natural products collection now in control of the Baruch S. Blumerg Institute, Doylestown, PA (formerly known as the Institute of Hepatitis Virus Research Labs (IHVR)). In one embodiment, the extract is obtained from *Actinomyces* species with a capacity to produce similar chemical composition as is produced by extract A5640. In another embodiment, the bacteria are collected in the USA and the strain is identical to previously assigned species A5640.

Compositions

In one embodiment, the method of the invention comprises applying to tissue in need of treatment a composition comprising a botanical or bacterial extract as described herein. Such tissue may be for example human skin, hair, nails, oral mucosa, nasal mucosa, or vaginal mucosa. Such tissue may be in need of treatment for or prevention of a disease or condition treatable or preventable by retinoids, preferably retinol.

Preferably, the methods of the invention comprise administering a composition comprising a safe and effective amount of an extract of the invention to the tissue in need of treatment. In the case of skin in need of anti-aging treatment, an anti-aging effective amount of such extract may be used.

In one embodiment, the methods comprise applying from greater than zero to about 20% by weight based on the total weight of the composition of extract to the tissue in need. In another embodiment, the methods comprise applying from about 0.0001 to about 20%, or about 0.001 to about 10%, or about 0.01 to about 5%, or about 0.1 to about 5%, or about to about 2%, by weight based on the total weight of the composition, of the extract to the tissue in need. In yet another embodiment, the methods comprise applying from greater than zero to about 1%, or about 0.0001 to about 1%, or about 0.001 to about 1%, or about 0.01 to about 1%, by weight based on the total weight of the composition, of extract to the tissue.

Any suitable carrier may be used in the compositions of the invention depending on the route of administration, i.e. whether topical, oral, buccal, intra-nasal, periodontal, or vaginal. Preferably, for a topical composition, the carrier is a cosmetically-acceptable carrier. As will be recognized by those of skill in the art, cosmetically-acceptable carriers are carriers that are suitable for use in contact with the body, for example in contact with the skin, hair or nails, without undue toxicity, incompatibility, instability, irritation, allergic response, and the like.

A safe and effective amount of carrier is used in the compositions. For example, the carrier may comprise from about 50% to about 99.999%, preferably from about 80% to about 99.9%, more preferably from about 99.9% to about 95%, most preferably from about 99.8% to about 98% of the composition. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cP to about 200,000 cP.

Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, makeup, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like.

The following are non-limiting examples of such carriers. Other carriers can be formulated by those of ordinary skill in the art. In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and non-ionic nature; vegetable oils; mineral oils; waxes; gums; synthetic and natural gelling agents; alkanols; glycols; and polyols. Examples of glycols include, but are not limited to, glycerin, propylene glycol, butylene glycol, pentylene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. In one embodiment solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 1673-1686.

Lotions and creams can be formulated as emulsions. Typically, such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The compositions of the invention can also be formulated into a solid formulation (e.g., a wax-based stick, soap bar composition, powder, or wipe). The composition of the invention can also be combined with a solid, semi-solid or dissolvable substrate (eg., a wipe, mask, pad, glove or strip).

The compositions of the invention may further comprise one or more additional cosmetically active agents. As used herein, a "cosmetically active agent" is a compound that has a cosmetic or therapeutic effect on human tissue such as skin, hair, nails, or mucosa.

Examples of suitable additional cosmetically active agents include skin lightening agents, darkening agents, anti-acne agents, shine control agents, anti-microbial agents such as anti-yeast agents, anti-fungal and anti-bacterial agents, anti-inflammatory agents, anti-parasite agents, external analgesics, sunscreens, photo-protectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like.

Examples of various suitable additional cosmetically acceptable actives include hydroxy acids, benzoyl peroxide, D-panthenol, UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, dipeptides, sugar amines, coenzyme Q10, amino acids such a proline, vitamins, lactobionic acid, acetyl-coenzyme A, niacin, riboflavin, thiamin, ribose, electron transporters such as NADH and FADH 2, and other botanical extracts such as oat, aloe vera, Feverfew, Soy, Shiitake mushroom extracts, and derivatives and mixtures thereof.

In one embodiment, the compositions of the invention are skin care compositions that comprise a botanical or bacterial extract as described herein, and at least one skin lightening active agent. Examples of suitable skin lightening active agents include, but are not limited to, tyrosinase inhibitors, melanin-inhibiting agents, melanosome transfer inhibiting agents including PAR-2 antagonists, exfoliants, sunscreens, retinoids, antioxidants, Tranexamic acid, skin bleaching agents, allantoin, opacifiers, talcs and silicas, zinc salts, and the like, and other agents as described in Solano et al. Pigment Cell Res. 2006, 19 (550-571). Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea* Coposita root extract, Saxifraga extract and the like, Ellagic acid, Salicylates and derivatives, Glucosamine and derivatives, Fullerene, Hinokitiol, Dioic acid, Acetyl glucosamine, Magnolignane, combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4alkyl-resorcinols such as 4-butyresorcinol (rucinol), 4-hexylresorcinol, phenylethyl resorcinol, 1(2,4-dihydroxyphenyl)-3-(2, 4-dimethoxy-3-methylphenyl)-Propane and the like and natural extracts enriched in resorcinols. Examples of salicylates include, but are not limited to, salicylic acid, acetyl-salicylic acid, 4-methoxysalicylic acid and their salts. In certain embodiments, the tyrosinase inhibitors include a 4-substituted resorcinol, a vitamin C derivative, or a vitamin E derivative. In yet another embodiment, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol, retinaldehyde, retinoic acid, retinyl palmitate, isotretinoin, tazarotene, bexarotene and Adapalene. In certain embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, feverfew, parthenolide-free feverfew, oat extracts, pomelo extract, wheat germ extract, Hesperidin, Grape extract, *Portulaca* extract, Licochalcone, chalcone, 2,2'-dihydroxy chalcone, *Primula* extract, propolis, and the like.

Examples of vitamins include, but are not limited to, vitamin A, vitamin Bs (such as vitamin B3, vitamin B5, and vitamin B12), vitamin C, vitamin K, and vitamin E, and derivatives thereof.

The additional cosmetically active agent may be present in a composition in any suitable amount, for example, in an amount of from about 0.0001% to about 20% by weight of the composition, e.g., about 0.001% to about 10% such as about 0.01% to about 5%. In certain embodiments, in an amount of 0.1% to 5% and in other embodiments from 1% to 2%.

A variety of other materials may also be present in the compositions of the invention. These include, for example, chelating agents, humectants, proteins, polypeptides, opacifiers, pigments, conditioners, preservatives, fragrances and the like. The compositions may include surfactants, for example, those selected from the group consisting of anionic, non-ionics, amphoteric, cationic, or a combination of two or more thereof.

The composition and products containing such compositions of this invention may be prepared using methodology that is well known by an artisan of ordinary skill.

In one embodiment, the invention comprises applying a compound or composition of the invention via a substrate comprising such material. Any suitable substrate may be used in the invention. Examples of suitable substrates and substrate materials are disclosed, for example, in U.S. Pat. No. 7,452,547 and U.S. Published Application No. 2009/0241242 which are incorporated herein by reference in their entirety.

In one embodiment, the substrate is a wipe or a facial mask. Such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval.

In one embodiment, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 $cm^2$ to about 200 $cm^2$, such as from about 120 $cm^2$ to about 160 $cm^2$ and the second water-insoluble substrate has a surface area of from about 100 $cm^2$ to about 300 $cm^2$, such as from about 150 $cm^2$ to about 250 $cm^2$. In one embodiment, the water-insoluble substrate has a low stiffness such that it may, for example, readily drape over or conform to the face or other body parts of the user.

The invention may comprise application to any skin in need of treatment on the human body. For example, application may be made to any one or more of the skin of the face, neck, chest, back, arms, axilla, hands and/or legs. In certain embodiments, the method comprises applying a botanical or bacterial extract as described herein to skin of the face.

Moreover, compositions may be applied to other tissues, including hair, nails, oral mucosa, nasal mucosa, or vaginal mucosa.

Any suitable method of applying the composition to the tissue in need may be used in accordance with the invention. For example, the composition may be applied directly from a package to the tissue in need, by hand to the tissue in need, or may be transferred from a substrate such as a wipe or mask, or a combination of two or more thereof. In other embodiments, the composition may be applied via a dropper, tube, roller, spray, patch or added to a bath or otherwise to water to be applied to the tissue, and the like.

In certain embodiments, the methods of the invention further comprise the step of contacting the composition with the tissue for period of time. For example, the composition is left in contact with the tissue for a period of about 15 minutes or greater. In another embodiment, the composition is left in contact with the tissue for about 20 minutes or greater, more preferably about 1 hour or greater.

In certain embodiments, the method of the invention comprises a regimen comprising applying the composition to tissue multiple times over a selected period of time.

For example, the invention provides a method of treating signs of aging comprising applying to skin in need of treatment for signs of skin aging a composition comprising an extract as described herein once or twice daily for at least 12 weeks, preferably at least 8 weeks and more preferably for at least 2 weeks.

In certain embodiments, the methods of the invention comprise applying at least two different compositions or products comprising botanical or bacterial extracts to the tissue. For example, the methods may comprise applying a first composition comprising an extract to tissue in need of treatment followed by applying a second composition comprising the same or different extract, to the skin in need of treatment. In certain embodiments, the first and second composition may be independently selected from the group consisting of lotions, cleansers, masks, wipes, creams, serums, gels, and the like. In certain embodiments, at least one of the first and second compositions is a cleanser, lotion, cream, essence, or serum and the other is a facial mask or wipe. In certain other embodiments, at least one of the first and second compositions is a cleanser and the other is a lotion or cream.

In certain other embodiments, the method comprises applying at least three products or compositions comprising an extract to tissue in need of treatment. Preferably such three products are selected from the group consisting of cleansers, lotions, creams, essences, and facial masks.

The compositions of this invention can also be formulated into an ingestible composition. As used herein, "ingestible composition" means a composition that is intended to be ingested or orally administered. Examples of forms of ingestible compositions include, but are not limited to, tablets, pills, capsules, powders, granules, solutions or suspensions, and drops. Such compositions may be swallowed whole or may be in chewable form. An "ingestible composition" may also be in the form of a confectionary or a food product such as a cookie, candy, food bar, chewing gum, yogurt additive, sprinkles, tea, juice or other drink, liquid shake or the like. Ingestible compositions do not include compositions intended to be topically administered to the skin or oral/vaginal cavity.

The composition can be used to treat a variety of skin diseases and conditions, such as reducing the appearance of skin aging, skin inflammation, and skin pigmentation.

Examples of skin aging that may be treated by topical or oral use of the compositions of this invention include, but are not limited to, wrinkles on the skin, loss of the firmness or elasticity of the skin, sagging, lax and loose tissue. As used herein, the term "wrinkle" includes fine line, fine wrinkles, coarse wrinkles, cellulite, scars, and stretch marks. Examples of wrinkles include, but are not limited to, fine lines around the eyes (e.g., "crow's feet"), forehead and cheek wrinkles, frown-lines, and laugh-lines around the mouth.

Examples of skin inflammation that may be treated by topical or oral use of the compositions of this invention include, but are not limited to, arthritis, contact dermatitis, atopic dermatitis, psoriasis, seborrheic dermatitis, eczema, allergic dermatitis, polymorphous light eruptions, inflammatory dermatoses, folliculitis, alopecia, poison ivy, insect bites, irritation induced by extrinsic factors including, but not limited to, chemicals, trauma, pollutants (such as cigarette smoke) and UV or wind exposure, and secondary conditions resulting from inflammation including but not limited to xerosis, hyperkeratosis, pruritus, post-inflammatory hyper-pigmentation, scarring and the like.

Examples of skin pigmentation that may be treated by topical or oral use of the compositions of this invention include, but are not limited to, skin hyper-pigmentation, light areas of the skin, uneven tone of the skin, discoloration and puffiness around the eye. Discoloration and puffiness around the eye include, but are not limited to, dark circles and bags under the eye. In one embodiment, the dark circles under the eye being treated are a result of the increase concentration of blood in the skin under the eye.

Topical uses of the compositions containing botanical or bacterial extracts described herein and a cosmetically acceptable carrier include for example aging of the human skin, dry skin, pigment defects, UV damages on the skin, skin unevenness, such as wrinkles, fine lines, rough skin or large-pored skin, and diseases associated with skin aging, such as defective keratinization, acne, eczema, inflammation, and skin atrophy.

As used herein, "topical use" and "topically applying" means directly laying on or spreading on the skin, hair, or nail, e.g., by use of the hands or an applicator such as a wipe.

In one embodiment, the invention is a method of treating a sign of skin aging comprising topically applying to skin in need of treatment for skin aging a safe and effective amount of composition comprising extract as described herein.

In another embodiment, the invention is a method of improving skin barrier properties, comprising topically applying to skin in need of improved skin barrier function and moisturization a composition comprising an extract as described herein.

In another embodiment, the invention is a method of treating acne, comprising topically applying to skin in need of treatment for acne a composition comprising an extract as described herein.

EXAMPLES

The following materials and test methods were used in the Examples.

Gene Expression Test Method

Abdominal skin samples were obtained from human adults undergoing abdominoplasty surgery. Informed consent was obtained from each patient, and all experimental steps were approved by an institutional review board (IRB). Subcutaneous fat was carefully removed and skin biopsies of 0.93 $cm^2$ were prepared under sterile conditions and acclimated in DMEM/F12 (1:1) medium, 2% heat-inactivated fetal bovine serum, 10 µg/mL insulin, 10 ng/mL hydrocortisone, 10 ng/mL EGF, 1×ABAM under a 5% $CO_2$ humidified atmosphere overnight. Skin explants were treated topically at various concentrations for 48 hours. At the end of the 48 h incubation, half of the skin biopsies were lysed in 400 µl lysis buffer, consisting of 100 parts RLT buffer (RNeasy Mini kit, Qiagen, Valencia, CA), to one part 2-mercaptoethanol inside a reinforced tube with screw cap and o-ring closure, and ceramic beads in the tube for tissue grinding (sold under the tradename PRECELLYS CKMix50-R, Bertin Corp, Rockville, MD). The tubes were shaken 40 sec at 6300 rpm. RNA was extracted from the solutions using the RNeasy Mini Kit (Qiagen, Valencia, CA) according to manufacturer's instructions and RNA was eluted in 25 µl RNase-free water.

Reverse transcription (RT) was performed using the Applied Biosystems High Capacity Reverse Transcription Kit (ThermoFisher Scientific, Bridgewater, NJ). Gene expression assays sold under the tradename TAQMAN for cellular retinoic acid binding protein 2 (CRABP2), heparin-binding epidermal growth factor (HbEGF), hyaluronic acid synthase 3 (HAS3), UDP-glucose ceramide glucosyltransferase (UGCG), polymerase (RNA) II polypeptide A (POLR2A), and master mix sold under the tradename TAQMAN were purchased from ThermoFisher Scientific (Bridgewater, NJ). qPCR analysis was performed using TaqMan® Master Mix (ThermoFisher Scientific, Bridgewater, NJ), and run on a real time PCR system sold under the tradename QUANTSTUDIO 7 Flex System (ThermoFisher Scientific, Bridgewater, NJ). The expression of these genes was normalized against the expression of the human POLR2A housekeeping gene. The fold changes were calculated in comparison to the untreated or vehicle controls and two-tailed two-sample Student t-tests (Microsoft Office Excel 2007; Microsoft, Redmond, WA, USA) were performed.

RARg Transactivation Assay Method

Retinoic acid receptor gamma (RARg) agonism was assessed using the Invitrogen GeneBLAzer RAR gamma-UAS-bla HEK 293T cell-based assay, in which activation of RARg results in transcription of beta lactamase. When a FRET probe is added to cells, FRET is observed. However, upon receptor activation and subsequent beta lactamase expression, the probe is cleaved and FRET is no longer observed.

Cells in culture are washed with PBS, trypsinized and resuspended in growth media, counted using ViCell cell counter; the appropriate amount of cells is then spun down and resuspended in assay buffer (at 0.5E6 cells/ml). 15 k cells in 30 ul assay buffer is plated per well in Greiner black walled, clear flat bottom plates using Combi dispenser. The last two columns are filled with assay buffer. 10 ul of 4× concentrated test samples is added to the cells using Janus dispenser, and cells are spun down at 800 rpm for 2 min without brakes and left at RT for 15 min prior to o/n incubation at 37° C.

After 18-20 h of incubation, 8 ul FRET dye (Invitrogen K1096) is added using Tempest dispenser, after which plates are spun down at 800 rpm for 2 min without brakes and incubated in the dark at room temperature for 2 h. The bottom of the plates is cleaned using anti-static cleaning wipe before measuring fluorescence using BMG Pherastar plate reader (using FRET module, 10 reads, gain for both channels=1000, Ex 409, Em1 460, Em2 530). Average Em1 and Em2 values from assay buffer only wells are subtracted from the test Em1 and Em2 values respectively, and subsequent determination of Em1/Em2 ratio represents RARg activity. DMSO and ATRA were used as neutral and stimulator controls respectively for normalization.

Extract of *Acronychia acidula* (E1)

A pre-weighed frozen fruit of *Acronychia acidula* was homogenized in a blender for 30 seconds with denatured alcohol in equal part to frozen fruit. The pulp was then mixed and stirred for another 24 hours at ambient temperature (22 to 26 degrees C.). Additional denatured alcohol was added as needed to keep the pulp covered well in alcohol. The mixture then was gravity filtered, and the filter cake was washed with additional amounts of denatured alcohol. The total filtrate then was dried under reduced pressure to remove alcohol. The residue was freeze dried to obtain dry matter free of extraction solvent and water. The extraction was repeated on the filter cake a few times with an extract yield of 5-7% regularly obtained from each extraction. One such batch was prepared using 100 kg of frozen fruit of Acronychia acidula and the dried extract (E1) was used in subsequent experiments described herein.

Extract of Licaria vernicosa (E2, E3)

Two extracts of Licaria vernicosa were obtained from the Baruch S. Blumerg Institute, Doylestown, PA (formerly known as IVHR). The first extract was from the woody part of the plant (E2) and the second extract was from the roots of the plant (E3). Within the nomenclature of IHVR collection, the extracts are labeled as IHVR_40256_G10=X-005348-001E002 and as IHVR_40256_E10=X-005346-001M002 respectively. The woody parts and the roots of Licaria vernicosa (Mez) Kosterm. were collected from Guyana. 504.3 g of dried, ground woody plant material was extracted with ample methanol, which was dried under vacuum to afford 10.54 g of crude methanol extract (E2) for X-005348-001E002. 403.8 g of dried, ground root material was extracted with ample methanol, which was dried under vacuum to afford 18.11 g of crude methanol extract (E3) for X-005346-001M002.

Extract of Actinomyces sp A5640 (E4)

A general method of culture and extraction of this strain and its extract is recorded with the Baruch S. Blumerg Institute, Doylestown, PA (formerly known as IVHR). Within the nomenclature of IHVR collection, the extract is labeled as IHVR_39565_F7. The extract of Actinomyces sp A5640 is referred to as E4 herein.

Extracts of Calendula officinalis (E5) and of Trigonella foenum-graecum (E6)

Extracts of Calendula officinalis (E5) and of Trigonella foenum-graecum (E6) were obtained from Caithness Biotechnologies Ltd, UK (http://www.caithnessbiotechnologies.com/). These extracts are part of The Phytotitre Natural Product Library available to everyone for purchase. The extracts preparation method is described by Caithness Biotechnologies Ltd. as non-polar using a mixture of methanol and methylene chloride. In a typical extraction a pre-weighed dried powdered biomass is suspended and stirred in a mixture of methanol/methylene chloride (1:1) over night at ambient temperature. The suspension is then filtered, and the filtrate is dried under reduced pressure to a residue free of solvents. The residue is then dissolved in sufficient amount of 100% DMSO to get a stock solution at a concentration of 10 mg/mL. Such a stock solution was used to make dilutions in appropriate media for screening.

Example 1

Gene expression analysis for CRABP2 was performed on compositions of 0.1% (w/v) of Acronychia acidula extract (E1), 0.1% (w/v) Licaria vernicosa extracts (E2 and E3), and (w/v) Actinomyces sp A5640 extract (E4), each in a 30/70 (v/v) polypropylene glycol/ethanol vehicle. Gene expression was performed according to the gene expression analysis test method described above. The test compositions were compared against 0.1% retinol product sold under the tradename NEUTROGENA RAPID WRINKLE REPAIR (RWR) (Johnson & Johnson Consumer Inc., Skillman NJ), untreated, and vehicle treatment. Results are shown in Table 1.

TABLE 1

|  | Untreated | Vehicle | RWR (0.1% retinol) | 0.1% E1 | 0.1% E2 | 0.1% E3 | 0.1% E4 |
| --- | --- | --- | --- | --- | --- | --- | --- |
| CRABP2 | 1.00 | 0.41 | 2.43 | 2.96 | 1.47 | 1.88 | 1.42 |

Results:

Cellular retinol binding proteins (CRABPs) are a family of cytoplasmic binding proteins that have been shown to facilitate the uptake of retinol and prevent retinol from spontaneous non-enzymatic isomerization and oxidation. It has been shown that CRABP2 (cellular retinoic acid binding protein-II) message was up-regulated by treatment with retinol in human skin, both in vivo and in vitro.

This example shows that topical treatment of human skin explants by the compositions of Acronychia acidula, Licaria vernicosa and Actinomyces sp A5640 extracts used at 0.1% (w/v) elicit retinol-like bioactivity, as shown by the induction of the expression of the gene of CRABP2. Therefore, the upregulation of CRABP2 and its associated retinol-like activity are indicative of the retinol-like related skin benefits for example improved skin appearance including reducing the signs of aging including reducing fine lines and reducing wrinkles.

Example 2

Gene expression analysis for CRABP2 was performed on compositions of 0.04% (w/v) to 3% (w/v) of Acronychia acidula extract (E1) in 30/70 (v/v) polypropylene glycol/ethanol vehicle according to the gene expression analysis test method described above. The test compositions were compared against 0.1% retinol product sold under the tradename NEUTROGENA RAPID WRINKLE REPAIR (RWR) and vehicle treatment. Results are shown in Table 2.

TABLE 2

|  | Vehicle | 0.04% E1 | 0.1% E1 | 1% E1 | 3% E1 | RWR (0.1% retinol) |
| --- | --- | --- | --- | --- | --- | --- |
| CRABP2 | 1 ± 0.1 | 2.35 ± 1.15 | 4.27 ± 0.44* | 7.20 ± 0.81* | 5.12 ± 1.50* | 6.22 ± 2.84* |

Results:

Cellular retinol binding proteins (CRABPs) are a family of cytoplasmic binding proteins that have been shown to facilitate the uptake of retinol and prevent retinol from spontaneous non-enzymatic isomerization and oxidation. It has been shown that CRABP2 (cellular retinoic acid binding protein-II) message was up-regulated by treatment with retinol in human skin, both in vivo and in vitro.

This example shows that topical treatment of human skin explants by the compositions of 0.04% (w/v) to 3% (w/v) of Acronychia acidula extract induced a retinoic-acid gene CRABP2 gene expression in human skin explants when applied topically *, p<0.05. The Acronychia acidula extracts elicit retinol-like bioactivity, as shown by the induction of the expression of the gene of CRABP2, similarly to the benchmark 0.1% RWR retinol used as assay positive control.

Example 3

Gene expression analysis for HAS3, UGCG and HbEGF was performed on a composition of 0.1% (w/v) of *Acronychia acidula* extract (E1) in 30/70 (v/v) polypropylene glycol/ethanol vehicle according to the gene expression analysis test method described above. The test compositions were compared against 0.1% retinol product sold under the tradename NEUTROGENA RAPID WRINKLE REPAIR (RWR) vehicle treatment, and untreated. Results are shown in Table 3.

The upregulation of these gene activities is indicative of the retinol-like related skin benefits for example improved skin appearance including reducing the signs of aging including reducing fine lines and reducing wrinkles. The upregulation of the UCGC genes leads to increased glycosylated ceramide formation that enhances epidermal lipid production which strengthens skin barrier.

TABLE 3

|  | Untreated | Vehicle | RWR (0.1% retinol) | 0.1% E1 |
| --- | --- | --- | --- | --- |
| HAS3 | 1 ± 0.0 | 1.58 ± 1.32 | 3.49 ± 1.73* | 2.60 ± 1.27* |
| HbEGF | 1 ± 0.0 | 1.35 ± 0.76 | 7.16 ± 2.69* | 6.18 ± 1.95* |
| UGCG | 1 ± 0.0 | 1.99 ± 1.07 | 4.60 ± 3.33 | 4.42 ± 2.15* |

Results:

Genes for heparin-binding epidermal growth factor (HbEGF) and hyaluronan synthase 3 (HAS3) are also induced by retinol. HbEGF is known to improve skin thickness, plumpness, and to reverse skin thinning due to steroid treatment while HAS3 is known to improve skin moisture. UGCG is an enzyme that in humans is involved in ceramide synthesis and is known to improve the skin barrier.

Example 3 shows that topical treatment of human skin explants by the compositions of 0.1% (w/v) *Acronychia acidula* extract induced HAS3, HbEGF, and ceramide glucosyltransferase (UGCG) gene expression similar to RWR, 0.1% retinol in human skin explants when applied topically *, p<0.05.

Figure 1:
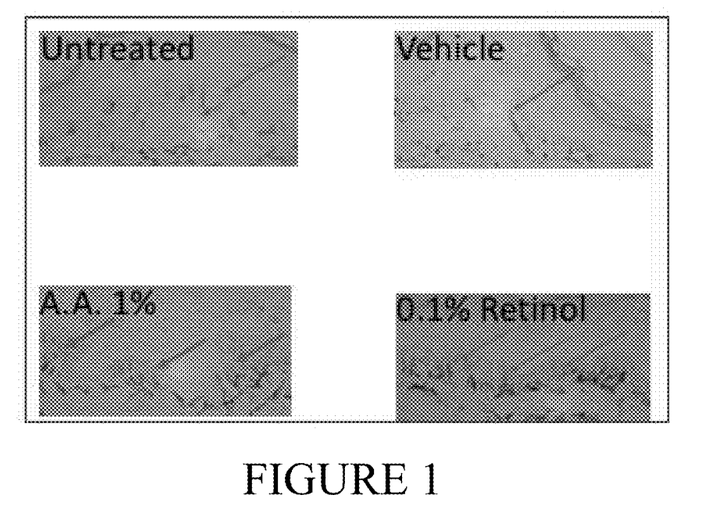
FIG. 1 are photographs of skin explants including untreated, treated with the vehicle, 1% *Acronychia acidula* extract (E1) and 0.1% retinol as described in Example 4.

Example 4 mm biopsies of human skin explants were treated topically with either a 30/70 (v/v) polypropylene glycol/ethanol vehicle alone, or a composition of 1% (w/v) of *Acronychia acidula* extract (E1) in 30/70 (v/v) polypropylene glycol/ethanol vehicle for seven days and its impact on the elastin fiber formation was investigated. In addition, Human skin explants were also treated topically with a formulation containing 0.1% retinol as a positive control. Moreover, samples of Human skin explants were left untreated as a negative control. After the 7 days, the skin biopsies were fixed in 10% buffered formalin solution (Thermo Fisher Scientific, Hudson, NH), dehydrated and then embedded in paraffin. Five micrometer-thick sections were collected from each biopsy. Sections were stained with Luna staining (American HistoLabs, Gaithersburg, MD), for documenting elastin fibers in purple color. Images of skin explants were obtained using Leitz microscope and a Leica camera (Leica, Allendale, NJ). FIG. 1 shows the images of the skin explants including untreated, treated with the vehicle, 1% *Acronychia acidula* extract (E1) and 0.1% retinol.

Results:

In contrast to untreated human skin samples or skin samples treated with a solution of 30/70 (v/v) polypropylene glycol/ethanol vehicle alone treated topically, an increase of elastin fiber formation was observed in the epidermal-dermal region of human skin explants treated topically with a composition of 1% (w/v) of *Acronychia acidula* extract (E1) in 30/70 (v/v) polypropylene glycol/ethanol vehicle for seven days, similarly to that observed with the formulation containing 0.1% retinol used as experimental positive control.

Increased elastin formation produces skin that is stronger had more elasticity and less prone to signs and symptoms of skin ageing for example wrinkle formation. Increased elastin fiber formation is a known retinol-induced anti-aging skin benefits associated with improved skin appearance including reducing the signs of aging including reducing fine lines and reducing wrinkles. Therefore, the increase of elastin fiber formation by the *Acronychia acidula* extract is a retinol-like activity and is indicative of the retinol-like related skin benefits for example improved skin appearance including reducing the signs of aging including reducing fine lines and reducing wrinkles.

Example 5

Figure 2:
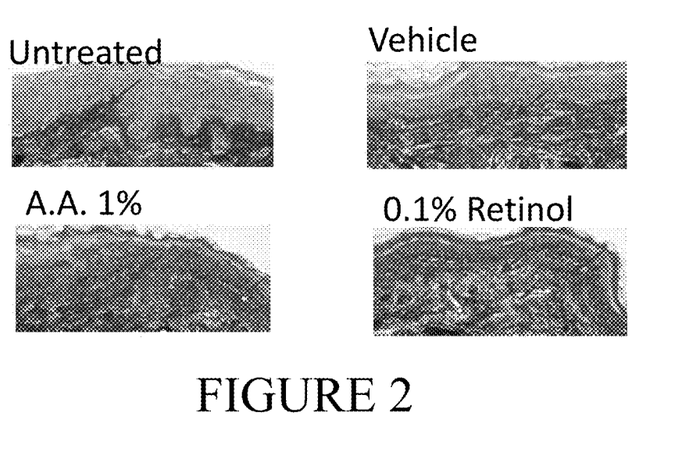
FIG. 2 are photographs of the skin explants including untreated, treated with the vehicle, 1% *Acronychia acidula* extract (E1) and 0.1% retinol as shown in Example 5.

10 mm biopsies of human skin explants were treated topically with either a 30/70 (v/v) polypropylene glycol/ethanol vehicle alone, or a composition of 1% (w/v) of *Acronychia acidula* extract (E1) in 30/70 (v/v) polypropylene glycol/ethanol vehicle for seven days and its impact on the elastin fiber formation was investigated. In addition, Human skin explants were also treated topically with a formulation containing 0.1% retinol as experimental positive control for comparison purposes. Moreover, samples of Human skin explants were left untreated as experimental negative control for comparison purposes. After the 7 days, the skin biopsies were fixed in 10% buffered formalin solution (Thermo Fisher Scientific, Hudson, NH), dehydrated and then embedded in paraffin. Five micrometer-thick sections were collected from each biopsy. Sections were stained with Herovici staining (American HistoLabs, Gaithersburg, MD), for documenting pro-collagen in blue color. Images of skin explants were obtained using Leitz microscope and a Leica camera (Leica, Allendale, NJ). FIG. 2 shows the images of the skin explants including untreated, treated with the vehicle, 1% *Acronychia acidula* extract (E1) and 0.1% retinol.

Results:

In contrast to untreated human skin samples or skin samples treated with a solution of 30/70 (v/v) polypropylene glycol/ethanol vehicle alone treated topically, an increase of pro-collagen formation was observed in the epidermal-dermal region of human skin explants treated topically with a composition of 1% (w/v) of *Acronychia acidula* extract (E1) in 30/70 (v/v) polypropylene glycol/ethanol vehicle for seven days, similarly to that observed with the formulation containing 0.1% retinol used as experimental positive control.

An increase in pro-collagen formation produces skin that is stronger, has more elasticity and less prone to signs and symptoms of skin ageing for example wrinkle formation and improves hydration and improves skin barrier function. Increase in pro-collagen formation is a known retinol-induced anti-aging skin benefit associated with improved skin appearance including reducing the signs of aging including reducing fine lines and reducing wrinkles. Therefore, the increase of pro-collagen formation by the *Acronychia acidula* extract is a retinol-like activity and is indicative of the retinol-like related skin benefits for example improved skin appearance including reducing the signs of aging including reducing fine lines and reducing wrinkles.

Example 6

A variety of extracts of *Calendula officinalis* (E5) and of *Trigonella foenum-graecum* (E6) were tested using the RARg Transactivation Assay at a concentration of 50 ug/ml on two separate days, with replicates on the first of the two days. Extracts providing a receptor activation of less than 15% were deemed inactive. Extracts providing a receptor activation of more than 25% were active.

The results are shown in Table 4.

TABLE 4

| Extract | Part of the plant used | Type of Extract | RARg Activity |
|---|---|---|---|
| E5 | Flowers | Polar | In-active |
| E5 | Petals | Polar | In-active |
| E6 | Leaves | Polar | In-active |
| E6 | Seed | Polar | In-active |
| E5 | Flowers | Non-polar | In-active |
| E5 | Petals | Non-polar | Active |
| E6 | Leaves | Non-polar | Active |
| E6 | Seed | Non-polar | In-active |

The non-polar extracts of *Calendula officinalis* petals and *Trigonella foenum-graecum* leaves in particular were significant RARg activators. In contrast, the other extracts from each of the two plants were found to be inactive when tested at a concentration of 50 ug/mL.

Subsequent dose response experiments using the RARg Transactivation Assay were performed on the two E5 and E6 active extracts as well as extracts of *Acronychia acidula* fruit (E1), *Licaria vernicosa* wood (E2), *Licaria vernicosa* root (E3) and *Actinomyces* bacteria (E4), which also had confirmed RARg activity via the RARg Transactivation Assay.

The results are shown in Table 5.

TABLE 5

| Extract | Source | Part of the plant used | Type of Extract | EC50 (ug/mL) |
|---|---|---|---|---|
| E5 | *Calendula Officinalis* | Petals | Non-Polar | 7.9 |
| E6 | *Trigonella foenum-graecum* | Leaves | Non-Polar | 13.5 |
| E1 | *Acronychia acidula* | Fruit | Non-Polar | 1.9 |
| E2 | *Licaria vernicosa* | Wood | Non-Polar | 21.9 |
| E3 | *Licaria vernicosa* | Root | Non-Polar | 32.2 |
| E4 | *Actinomyces* sp A5640 | (Cell Culture) | Non-Polar | >100 |

Effects of the extracts on cell viability were assessed, with no toxicity observed.

Example 7

The compound 3-(4-farnesyloxyphenyl)-propionic acid was tested using the RARg Transactivation Assay as follows.

The 3-(4-farnesyloxyphenyl)-propionic acid was manufactured by Organix Inc., a Woburn, Massachusetts, USA company. A routine synthetic scheme was followed to obtain 100 mg compound at a purity of >98%. All spectroscopic data confirmed the structural configuration for 3-(4-farnesyloxyphenyl)-propionic acid.

The compound was tested as a solution in DMSO at different concentrations to assess the EC50 value, which was found to be 0.22 ug/mL.

Example 8

The effect 3-(4-farnesyloxyphenyl)-propionic acid on skin hyperatinization was tested as follows.

Human epidermal skin equivalents from MatTek Company (Ashland, MA, USA) were used. The skin equivalents were topically treated with 10% oleic acid (OA) either without or with the addition of 1 µM 3-(4-farnesyloxyphenyl)-propionic acid in a proprietary MatTek medium (phenored free, hydrocortisone free) for 48 hours. The epidermal skin equivalents were collected at the end of treatment and fixed in 10% neutral buffered formalin solution (Thermo Fisher Scientific, Hudson, NH, USA), dehydrated and embedded in paraffin. Tissue sections (5 µm thick) were cut and were stained with hematoxylin-eosin. Three pictures per section were taken for each skin equivalent. The thickness of the stratum cornea or epidermis was measured using ImagePro Plus (Media Cybernetics Inc., Rockville, MD, USA). The stratum corneum thickness was expressed as % of total epidermis (=thickness of stratum corneum divided by the sum of thicknesses of stratum corneum and epidermis). The % hyperkeratinizatin was normalized by the thickness of 10% OA-treated tissues. Statistical analysis was performed using two-tailed two-sample equal variance Student t test (Microsoft Office Excel 2007; Microsoft, Redmond, WA, USA).

The results are shown in Table 6.

TABLE 6

| Test Composition | Stratum Corneum Thickness (% of Total Epidermis) | | % Hyperkeratinization (normalized by 10% OA) | |
|---|---|---|---|---|
| | Average | Standard Deviation | Average | Standard Deviation |
| 10% oleic acid | 50% | 9% | 100% | 17% |
| 10% oleic acid + 1 uM 3-(4-farnesyloxyphenyl)-propionic acid | 38% | 7% | 76% | 8% |

The results indicate 3-(4-farnesyloxyphenyl)-propionic acid significantly (p<0.05) reduced oleic-acid (OA) induced hyperkeratinization in human epidermal skin equivalents.

Acne vulgaris is a disease of pilosebaceous units with multifactorial pathogenesis, including hyperkeratinization. Excess unsaturated free fatty acids in sebum of acne subjects may contribute to impaired skin barrier associated with the increased follicular stratum corneum thickness and inflammation seen in acne. It is known that oleic acid may induce hyperkeratinzation in human epidermal skin equivalents mimicking acne pathohistology (Li, 2017). Accordingly, compositions according to the invention containing 3-(4-farnesyloxyphenyl)-propionic acid may be advantageously used to treat acne and other conditions associated with hyperkeratinzation.

We claim:
1. A method, comprising:
  identifying skin with the presence of lines and wrinkles and/or loss of elasticity due to diminished synthesis of collagen or elastin,
  topically applying to the skin a composition comprising a vehicle and a safe and effective amount of an agent that is 3-(4-farnesyloxyphenyl)-propionic acid and/or an ethyl ester thereof to elicit retinol-like bioactivity, and wherein the application of the agent to the skin upregulates at least one of:
(a) cellular retinoic acid binding protein-II (CRAPB2),
(b) hyaluronic acid synthase 3 (HAS3),
(c) heparin-binding epidermal growth factor (HbEGF), or
(d) UDP-glucose ceramide glucosyltransferase (UGCG),
on the order of a 0.1% retinol composition.

2. The method of claim 1, wherein the composition is substantially free of retinol.

3. The method of claim 1, wherein the application of the agent upregulates CRABP2 on the order of a 0.1% retinol composition.

4. The method of claim 3, wherein the application of the agent upregulates CRABP2 by about 2-7 as compared to the vehicle alone.

5. The method of claim 4, wherein the application of the agent upregulates CRABP2 by 3.38 to 9.06 as compared to the vehicle alone.

6. The method of claim 4, wherein the application of the agent upregulates CRABP2 by about 2.96 or about 2.43 as compared to an untreated control.

7. The method of claim 1, wherein the application of the agent upregulates HAS3 on the order of a 0.1% retinol composition.

8. The method of claim 7, wherein the application of the agent upregulates HAS3 by about 1.33 to 5.22 as compared to an untreated control.

9. The method of claim 7, wherein the application of the agent upregulates HAS3 by 1.33 to 3.87 or 1.76 to 5.22 as compared to an untreated control.

10. The method of claim 1, wherein the application of the agent upregulates HbEGF on the order of a 0.1% retinol composition.

11. The method of claim 10, wherein the application of the agent upregulates HbEGF by about 4.23 to 9.85 as compared to an untreated control.

12. The method of claim 10, wherein the application of the agent upregulates HbEGF by 4.23 to 8.13 or 4.47 to 9.85 as compared to an untreated control.

13. The method of claim 1, wherein the application of the agent upregulates UGCG on the order of a 0.1% retinol composition.

14. The method of claim 13, wherein the application of the agent upregulates UGCG by about 1.27 to 7.93 as compared to an untreated control.

15. The method of claim 13, wherein the application of the agent upregulates UGCG by 2.27 to 6.57 or 1.27 to 7.93 as compared to an untreated control.

16. The method of claim 1, wherein the 3-(4-farnesyloxyphenyl)-propionic acid and/or the ethyl ester thereof is from an extract of *Acronychia acidula*.

17. The method of claim 1, wherein the 3-(4-farnesyloxyphenyl)-propionic acid and/or the ethyl ester thereof is synthetically manufactured.

18. The method of claim 1, wherein the skin is free of a skin lightening disorder.

19. A method, comprising:
identifying skin with the presence of lines and wrinkles and/or loss of elasticity due to diminished synthesis of collagen or elastin,
topically applying to the skin a composition comprising a vehicle and 3-(4-farnesyloxyphenyl)-propionic acid and/or an ethyl ester thereof to elicit retinol-like bioactivity, and
wherein the application of the 3-(4-farnesyloxyphenyl)-propionic acid and/or an ethyl ester thereof increases pro-collagen formation in the epidermal-dermal region on the order of a 0.1% retinol composition.

* * * * *